United States Patent [19]

McCall et al.

[11] Patent Number: 5,281,597
[45] Date of Patent: Jan. 25, 1994

[54] HETEROCYCLIC AND AROMATIC THIOSEMICARBAZONES USEFUL IN THE TREATMENT OF FILARIASIS

[75] Inventors: John W. McCall, Athens, Ga.; Daniel L. Klayman, Chevy Chase, Md.; Ai Jeng Lin, Gaithersburg, Md.; Kenneth E. Kinnamon, Rockville, Md.; Max Grögl, Brookeville, Md.

[73] Assignee: The United States of America as represented by the Secretary of the Army, Washington, D.C.

[21] Appl. No.: 794,084

[22] Filed: Nov. 8, 1991

Related U.S. Application Data

[63] Continuation of Ser. No. 478,313, Feb. 12, 1990, abandoned.

[51] Int. Cl.⁵ .................. A61K 31/495; A61K 31/505; A61K 31/435; A61K 31/47
[52] U.S. Cl. .................................... 514/255; 514/256; 514/277; 514/311; 514/365; 514/427; 514/582
[58] Field of Search ................ 514/357, 255, 256, 277, 514/311, 365, 427, 582

[56] References Cited

U.S. PATENT DOCUMENTS 4,978,670 12/1990 Rector et al. ...................... 514/357

Primary Examiner—Zohreh A. Fay
Attorney, Agent, or Firm—Anthony T. Lane; Werten F. W. Bellamy

[57] ABSTRACT

This invention is directed to heterocyclic and aromatic thiosemicarbazones useful in the treatment of filariasis and in an animal, including humans.

7 Claims, No Drawings

HETEROCYCLIC AND AROMATIC THIOSEMICARBAZONES USEFUL IN THE TREATMENT OF FILARIASIS

This is a continuation, of application Ser. No. 07/478,313, filed Feb. 12, 1990, now abandoned.

BACKGROUND OF THE INVENTION

The helminthic diseases known collectively as filariasis, affect both humans and animals and are caused by a nematode parasite. The adult filarial worms (macrofilariae) live in the lymphatic system, tissues and body cavities of the vertebrate host. The female produces partially embryonated eggs which contain embryos that uncoil and become microfilariae. An effective drug should cause the death of either the macro- or the microfilariae and, preferably, both forms. Chemotherapeutic agents that can effectively damage or destroy either the microfilarial or the adult stages of filarial worms that infect man have been available for several decades. However, treatment remains problematic because the drugs cause adverse affects to the host and they inhibit or destroy either the adult worms or the microfilariae, but not both.

This invention utilizes heterocyclic and aromatic thiosemicarbazones to eliminate macro- and/or microfilariae. The most effective of the series is filarizone (Code No. BK49685 in the Table) which completely destroys both macro- and microfilarae of *Acanthocheilonoma viteae* and macrofilariae of *Brugia pahagi* at therapeutic dose levels without causing apparent toxicity to the host.

DETAILED DESCRIPTION OF THE INVENTION

This invention relates to the use of composition of matter and their pharmaceutically-acceptable acid addition salts in the treatment of filariasis in an animal comprising a therapeutically-effective amount of:

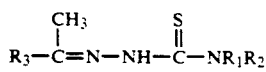

or a pharmaceutically-acceptable acid addition salt thereof wherein $R_1$ is hydrogen, alkyl, preferably having 1 to 12 carbon atoms or are, preferably 6 to 12 carbon atoms; cycloalkyl, preferably having 3 to 10 carbon atoms; substituted alkyl wherein the alkyl group preferably has 1 to 12 carbon atoms and the substituent group is amine, alkylamine (preferably 1 to 4 carbon atoms in each alkyl group), cycloalkyl (preferably 3 to 10 carbon atoms), hydroxy, C(O))alkyl (preferably 1 to 4 carbon atoms in the alkyl group), phenyl, or pyridyl; alkenyl, preferably having 2 to 6 carbon atoms; substituted benzyl wherein the substituent is methyl or phenyl on the alpha carbon atom, or the substituent is alkyl (preferably methyl), dialkyl (preferably dimethyl), halo, dihalo, or alkoxy (preferably ethoxy) on the phenyl ring; adamantyl; phenyl; naphthyl; substituted phenyl or substituted naphthyl wherein the ring is mono-, di-, or trisubstituted and the substituents are alkyl (preferably 1 to 4 carbon atoms), halo (preferably fluoro), alkoxy (preferably 1 to 4 carbon atoms), hydroxy, phenoxy, trifluoromethyl, dialkyl (preferably diethylaminomethyl) or C(O)Oalkyl (preferably 1 to 4 carbon atoms in the alkyl group); pyridyl; thienyl; indolyl; furyl; acridyl; quinolyl; or pyridazinyl.

$R_2$ is hydrogen or is selected from the group of radicals listed above for $R_1$, in which case $R_1$ and $R_2$ may be the same or diferent; and $R_3$ is pyridinyl; quinolinyl; pyrryl; thiazyl; 1,3-diazinyl-2-yl; 1,4-diazinyl-2-yl and phenyl; or $R_1$ and $R_2$ are taken together with the nitrogen atom to which they are attached to form a heterocyclic ring selected from the group consisting of:

(1) alkylenimino;

(2) alkylenimino which may contain one double bond and/or is mono- or disubstituted with alkyl (preferably 1 to 4 carbon atoms), hydroxy, phenyl, or benzyl;

(3) alkylenimino which is either bridged by an alkylene group (preferably 2 carbon atoms) or is fused to a phenyl ring; or is attached by a spiro linkage to an ethylene ketal group;

(4) homopiperazinyl; homopiperazinyl substituted with alkyl (preferably 1 to 4 carbon atoms); piperazinyl; or piperazinyl substituted with alkyl (preferably 1 to 4 carbon atoms), dialkyl (preferably 1 to 4 carbon atoms in each alkyl group), phenyl, C(O)Oalkyl (preferably 1 to 4 carbon atoms in the alkyl group), trifluoromethylphenyl, halophenyl, benzyl, or pyridinyl; and (5) morpholino, dialkyl (preferably 1 to 4 carbon atoms in each alkyl group) morpholino.

When $R_1$ and $R_2$ are taken together with the nitrogen atom to which they are attached, the resulting heterocyclic ring is preferably one of the following: azetidino; pyrrolidino; 2,5-dimethylpyrrolidino; piperidino;

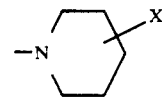

(wherein X is 2-methyl, 3-methyl, 4-methyl, 2-ethyl, 4-hydroxy, 4-phenyl, or 4-benzyl); hexamethylenimino; octamethylenimino; dodecamethylenimino; 2,6-dimethylpiperidino; 3,5-dimethyl piperidino; morpholino; 3,5-dimethylmorpholino;

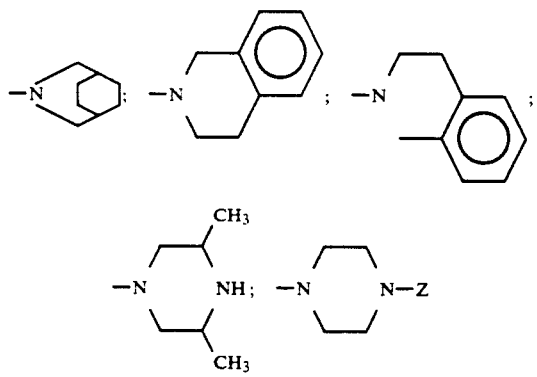

(wherein Z is methyl, phenyl, 3-trifluoromethylphenyl, benzyl, C(O))Et, 3-pyridinyl, 2-pyridinyl, or 4-fluorophenyl);

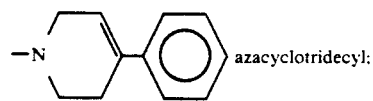

azacyclotridecyl;

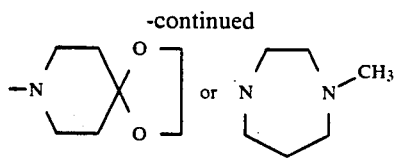

pharmaceutically-acceptable suspension medium (vehicle).

In this disclosure, it is understood the C(O)Oalkyl represents the alkyl carboxylic acid ester; for example, C(O)OEt represents the ethyl carboxylic acid ester.

A partial recitation of specific antifilarial heterocyclic or aromatic thiosemicarbazones contemplated within the scope of applicants, invention is depicted by the following formula: wherein R represents:

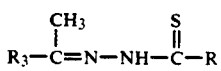

1. 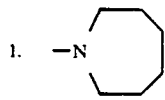

2. 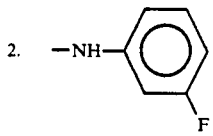

3. 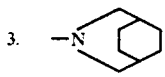

4. 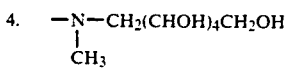

5. —N(CH$_3$)$_2$

6. 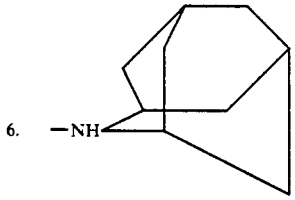

7. 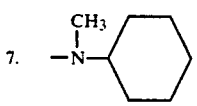

8. —NHCH$_3$

9. —NH$_2$

10. 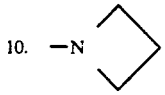

11. 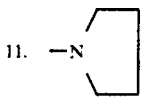

12. 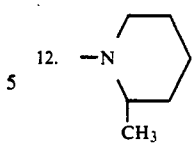

13. 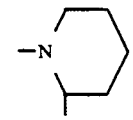

14. 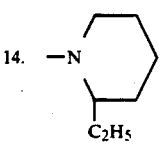

15. 

16. —NH—CH$_2$—CH=CH$_2$

17. 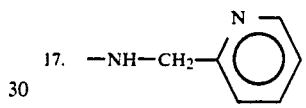

18. 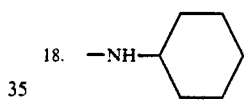

19. 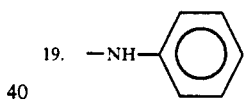

20. —NHC(CH$_3$)$_2$CH$_2$C(CH$_3$)$_3$

21. 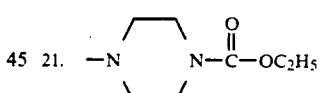

22. 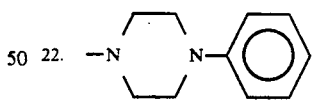

23. 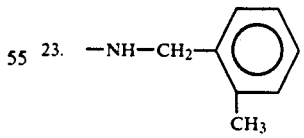

24. 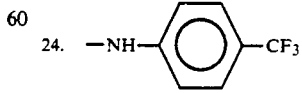

25. 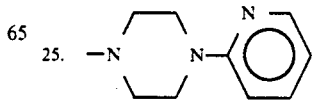

26. 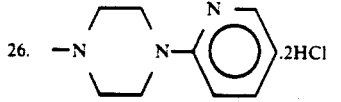

27. 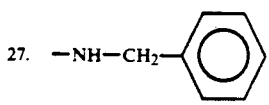

28. 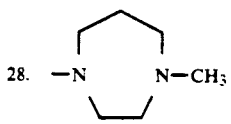

29. 

30. 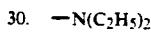

31. —NHCH$_2$CH$_3$

32. —NHC$_4$H$_9$

33. —NHC$_8$H$_{17}$

34. —NHC$_{10}$H$_{21}$

35. 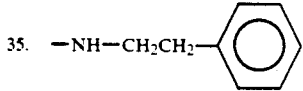

36. 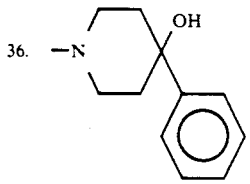

37. 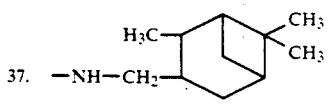

38. 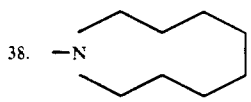

39. 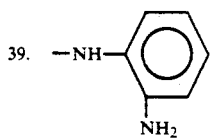

40. —NHCH$_2$CH$_2$NH$_2$

41. 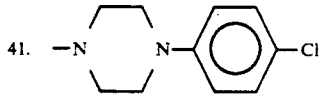

The chemical nomenclature for the antifilarial heterocyclic and aromatic thiosemicarbazones depicted in the preceding paragraph is as follows:

1. 1-Azacycloheptane-1-thiocarboxylic acid 2-1-(2-pyridinyl)ethylidene hydrazide
2. 2-Acetylpyridine 4-(3-fluorophenyl)-3-thiosemicarbazone
3. 3-Azabicyclo[3.2.2]nonane-3-thiocarboxylic acid 2-1-(2-pyridyl)ethylidene hydrazide
4. 1-Methylamino-1-deoxy-D-glucitol-N-thiocarboxylic acid 2-1-(2-pyridinyl)ethylidene hydrazide
5. 2-Acetylpyridine 4,4-dimethylthiosemicarbazone
6. 2-Acetylpyridine 4-(1-adamantyl)thiosemicarbazone
7. 2-Acetylpyridine 4-cyclohexyl-4-methyl-3-thiosemicarbazone
8. 2-Acetylpyridine 4-methyl-3-thiosemicarbazone
9. 2-Acetylpyridine thiosemicarbazone
10. Azetidine-1-thiocarboxylic acid 2-[1-(2-pyridinyl)ethylidene]hydrazide
11. 1-Azacyclopentane-1-thiocarboxylic acid 2-[1-(2-pyridinyl)ethylidene]hydrazide
12. Piperidine-1-thiocarboxylic acid 2-[1-(2-pyridinyl)ethylidene]hydrazide
13. 2-Methylpiperidine-1-thiocarboxylic acid 2-[1-(2-pyridinyl)ethylidene]hydrazide
14. 2-Ethylpiperidine-1-thiocarboxylic acid 2-[1-(2-pyridinyl)ethylidene]hydrazide
15. 1-Azacyclotridecane-1-thiocarboxylic acid 2-[1-(2-pyridinyl)ethylidene]hydrazide
16. 2-Acetylpyridine 4-allyl-3-thiosemicarbazone
17. 2-Acetylpyridine 4-(2-picolyl)-3-thiosemicarbazone
18. 2-Acetylpyridine 4-cyclohexyl-3-thiosemicarbazone
19. 2-Acetylpyridine 4-phenyl-3-thiosemicarbazone
20. 2-Acetylpyridine 4-(1,1,3,3-tetramethylbutyl)-3-thiosemicarbazone
21. 1,4-Diaza-4-carboethoxycyclohexane-1-thiocarboxylic acid 2-[1-(2-pyridinyl)ethylidene]hydrazide
22. 1,4-Diaza-4-phenylcyclohexane-1-thiocarboxylic acid 2-[1 (2-pyridinyl)ethylidene]hydrazide
23. 2-Acetylpyridine 4-(2-methylbenzyl)-3-thiosemicarbazone
24. 2-Acetylpyridine 4-(4-trifluoromethylphyenyl)-3-thiosemicarbazone
25. 1,4-Diaza-4-(2-pyridinyl)cyclohexane-1-thiocarboxylic acid 2-[1-(2-pyridinyl)ethylidene]hydrazide
26. 1,4-Diaza-4-(2-pyridinyl)cyclohexane-1-thiocarboxylic acid 2-[1-(2-pyridinyl)ethylidene]hydrazide dihydrochloride
27. 2-Acetylpyridine 4-benzyl-3-thiosemicarbazone
28. 1,4-Diaza-4-methylcycloheptane-1-thiocarboxylic acid 2-[1-(2-pyridinyl)ethylidene]hydrazide
29. 2-Acetylpyridine 4-(2-propynyl)-3-thiosemicarbazone
30. 2-Acetylpyridine 4,4-diethy-3-thiosemicarbazone
31. 2-Acetylpyridine 4-ethyl-3-thiosemicarbazone
32. 2-Acetylpyridine 4-butyl-3-thiosemicarbazone
33. 2-Acetylpyridine 4-octyl-3-thiosemicarbazone
34. 2-Acetylpyridine 4-decyl-3-thiosemicarbazone
35. 2-Acetylpyridine 4-(2-phenethyl)-3-thiosemicarbazone
36. (4-Hydroxy-4-phenylpiperidine)-1-thiocarboxylic acid 2-[1-(2-pyridinyl)ethylidene]hydrazide
37. 2-Acetylpyridine 4-(3-pinylmethyl)-3-thiosemicarbazone
38. 1-Azaclononane-1-thiocarboxylic acid 2-[1-(2-pyridinyl)ethylidene]hydrazide By "therapeutically-effective amount", as used herein, is meant a sufficient amount of the composition to provide the desired destruction of macro- and/or microfilariae at a reasonable benefit/risk ratio attendant any medical treatment. Within the scope of sound medical judgment, the amount of pharmaceutically active composition used will vary with the particular condition being treated, the severity of the condition, the duration of the treatment, the specific compound employed, its concentration, the condition of the patients, concurrent therapies being administered, and like factors within the specific knowledge and expertise of the patient or the attending physician.

By "pharmaceutically-acceptable", as used herein, is meant an inert suspension medium such as 0.5% hydroxyethylcellulose and 0.1% Tween or acid addition salts of 2-acetylpyridine thiosemicarbazones, as well as the other compatable drugs, medicaments or inert ingredients which the term describes that are suitable for use in the treatment of filariasis in humans and lower animals without undue toxicity, irritation, allergic response, and the like, commensurate with a reasonable benefit/risk ratio.

By the term "comprising", as used herein, is meant that various other compatible drugs and medicaments, as well as inert ingredients can be conjointly employed in the compositions and processes of this invention, as long as the heterocyclic or aromatic thiosemicarbazone is used. The term "comprising" thus encompasses and includes the more restrictive terms "consisting of" and "consisting essentially of" which characterize the use of the essential ingredients in the manner disclosed herein.

By the term "heterocyclic", as used herein, is meant pyridine, quinoline; pyrrole; thiazole; 1,3-diazine; or 1,4-diazine.

An essential component of the compositions of the present invention is a therapeutically-effective amount of a heterocyclic thiosemicarbazone or a pharmaceutically-acceptable acid addition salt thereof. Based on the weight of the total composition (the 2-acetylpyridine thiosemicarbazone and suspension medium (vehicle), the vehicle (medium) is present in an amount from about 95 to about 99.9% by weight; more preferably about 97 to about 99.9% by weight; most preferably 99.3% by weight.

The compositions of the present invention may additionally contain other adjunct components conventionally found in pharmaceutical compositions, at their art-established usage levels. Thus, for example, the compositions may contain additional compatible pharmaceutically-active materials which enhance antifilarial effectiveness or facilitates combination therapy (such as potentiating agents, antivirals, antimicrobials, antipruritics, astringents, local anesthetics or anti-inflammatory agents), or may contain materials useful in physically formulating various dosage forms of the composition of present invention, such as excipients, preservatives, antioxidants, thickening agents and stabliziers. These materials, when added, should not unduly interfere with the effectiveness of the compositions of this invention.

By the term aromatic, as used herein, is meant phenyl or substituted phenyl.

It can be seen from the foregoing that the compositions of the present invention admit to considerable variation, so long as the critical components, are a heterocyclic or aromatic thiosemicarbazone and an inert suspension medium, are present within the amounts indicated above and any undesirable affect on the therapeutic-effectiveness of the compositions of this invention are minimized.

The above-described heterocyclic or aromatic thiosemicarbazone compounds or their pharmaceutically-acceptable acid addition salts are dissolved in an inert suspension vehicle (medium) to form compositions which are useful in the treatment of filariasis caused by a nematode parasite.

With respect to the pharmaceutically-acceptable acid addition salts of this invention, it will be apparent to those of ordinary skill in the art that such salts are contemplated only where the structural features of the compounds permit their preparation. As non-limiting examples of acids used to prepare such salts, hydrochloric and hydrobromic acids are representative.

Synthetic Procedures

Three synthetic procedures proved to be useful for preparing the thiosemicarbazones of this invention. In Scheme A, a primary amine was converted to the corresponding isothiocyanate (1), ordinarily by employing thiophosgene. Reaction of 1 with hydrazine afforded a thiosemicarbazide 2. Condensation of this intermediate with 2-acetylpyridine provided the 4-monosubstituted thiosemicarbazone 3. However, only thiosemicarbazones monosubstituted at position 4 can be prepared in this manner, Scheme A

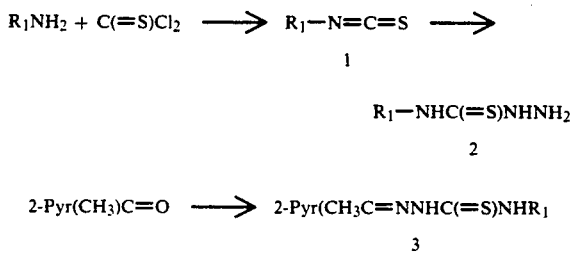

as 2-acetylpyridine proved to be usually resistant to condensation with 2,4-disubstituted thiosemicarbazides.

In Scheme B, reaction of hydrazine and carbon disulfide in the presence of sodium hydroxide yielded a carbodithioate. Alkylation of this carbodithioate with either iodomethane or dimethyl sulfate gave methyl hydrazinecarbodithioate (4). Condensation of 4 with 2-acetylpyridine gave the versatile intermediate, methyl 3-[1-(2-pyridinyl)ethylidene]hydrazine-carbodithioate, 5. Reaction of 5 with primary amines gave 4-monosubstituted thiosemicarbazones such as 3 while secondary amines or cyclic amines produced 4,4-disubstituted thiosemicarbazones, 6. In addition, reaction of 5 was not limited to more active nucleophiles, as excellent yields could be obtained with many primary aromatic amines. However, 5 was resistant to reaction with some secondary aromatic amines, such as N-methylaniline.

Scheme B

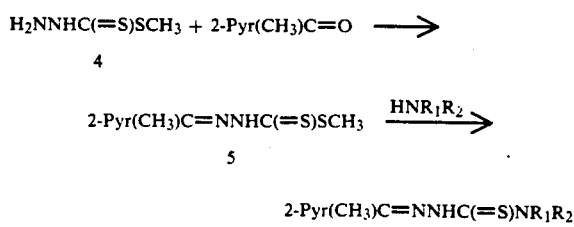

Scheme C involved the reaction of 2-acetylpyridine with hydrazine to yield the hydrazone 7. Reaction of this hydrazone with an isothiocyanate 1 produced a 4-monosubstituted thiosemicarbazone 3. This reaction was especially useful when the required isothiocyanate was commercially available.

Scheme C

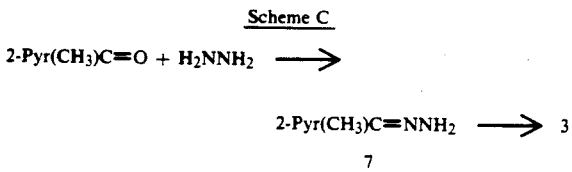

EXAMPLES

The working examples set forth below illustrate, without any implied limitation, the preparation of representative compounds and salts useful in the practice of this invention in the treatment of filariasis.

PROCEDURE, MATERIALS AND METHODS
PROCEDURE (Filaricidal Evaluation)

Potential filaricidal compounds were tested for therapeutic activity. At the primary level, compounds were routinely evaluated for macrofilaricidal activity against *Brugia pahangi* and *Acanthocheilonema viteae* and for microfilaricidal activity against *A. viteae* using dual infections of these filariae in jirds (*Merionis unguiculatus*). Subsequently, secondary testing of selected active compounds were done using either dual infections of *B. pahangi* and *A. viteae* or single infections of *B. pahangi* or *A. viteae*. Tertiary screening was done using lymphatic infections of *B. pahangi* in jirds. The compounds were suspended in hydroxyethylcellulose (0.5%) and Tween 80 (0.1%) by sonication of 20 kc for 10 minutes.

The primary screening model used is a dual infection of *B. pahangi* and *A. viteae*. In this system, compounds were evaluated for macrofilaricidal activity against *B. pahangi* (in the peritoneal cavity) and *A. viteae* (in subcutaneous tissue and between facial planes of muscles) and for microfilaricidal activity against *A. viteae*. Infections were established by subcutaneous transplantion of *A. viteae* adults and by transplantation of adult *B. pahangi* into the peritoneal cavity of jirds. Four jirds per test group were used. At least one, if not both, of these filarae is sensitive to all of the known macrofilaricidal (positive controls), and *A. viteae* microfilariae are sensitive to most of the known microfilaricides (positive controls).

Further secondary testing (e.g., dose titration) of specified types of compounds (e.g. thiosemicarbazones) was done against only intraperitoneal adult *B. pahangi* infections by oral, as well as subcutaneous administration of the compound. Their activity against lymphatic infections in jirds was also ascertained.

CHEMICALS

The Walter Reed Bottle Numbers and chemical structure relationships of the tested thiosemicarbazones are shown in Table I.

TEST TREATMENT

In this study, male Mongolian jirds weighing 50-60 grams were used. *B. pahangi* was maintained by alternate passage through Beagle dogs and *Aedes aegypti* (selected Liverpool strain) and *A. viteae* was cyclically maintained in jirds and the soft tick, *Ornithodoros tartakovskyi*, as described by McCall in the Journal of the Georgia Entomology Society Vol. 16, pages 283 to 293 (1981).

The exact dosage level used depended upon the sample size and toxicity of the drug. Compounds were given once daily at 100 mg/kg/day (MKD) for 5 days (X5) by subcutaneous injection, unless indicated otherwise. If sufficient amount of a compound was available, information concerning toxicity of the compound prior to treatment was obtained using non-infected jirds (one animal/compound tested) given a single dose (either orally or subcutaneously) of 200 mg/kg on a Friday. If no toxicity (death or excessive weight loss) was noted, treatment was begun at 100 MKD×5 the following Monday. If toxicity was noted, the dosage was adjusted accordingly.

For each therapeutic test experiment, each of 80 jirds was given 5 male and 5 female adult worms of *A. viteae* by subcutaneous transplantation. One to 2 weeks later, each animal recieved 10 male and 10 female *B. pahangi* by transplantation into the peritoneal cavity as described by Suswillo and Denham in the Journal of Parasitology. Vol. 673, page 591 (1977). One to 2 weeks later (on a Friday), 68 of these jirds were allocated to 17 test groups, each containing 4 jirds, and a control group of at least 6 jirds. On the following Monday (day 0), pretreatment microfilaremia levels were determined by spreading a 20 cm sample of ocular blood over a 20 mm × 15 mm area of a slide in a drop of water. The slide was immediately placed on a level surface, allowed to dry overnight and then stained with Giemsa stain. The number of microfilariae were counted to a total count of at least 200 per slide and the number of fields noted (a minimum of 5 fields were counted). Since there are 1.43 cm per 10 fields on the calibrated scope, the number of micrifilariae per cm was calculated. On the same day, dosing was initiated. The drug was given once daily for the ensuing 4 days unless toxicity was noted and weights were recorded on days 0, 1, 2, 3, and 4 and weekly thereafter. A compound was considered toxic if death occurred or if there was a 15% (group mean) weight loss. Microfilaremia levels were determined on day 4 to evaluate the microfilaricidal activity against *A. viteae* and again on day 56 to determine if the drug either sterilized or killed the adult worms. On days 50-60, all jirds were killed for determination of drug effects against the adults of *A. viteae* and *B. pahangi* in the skin and peritoneal cavities, respectively. The live worms were identified to species, noted as the sex and counted. The number of dead and/or encapsulated worms was recorded. After determining the number of microfilaria per cm, the data were stored and statistically analyzed using an Ohio Scientific C3-OEM computer. Microfilaremia and adult worm data were statistically analyzed using the Student's t test. A compound was considered active when the microfilaremia or adult worm burden in the test group was significantly lower (5% level) than that in the controls. In addition, a 90% reduction in microfilaremia, a 60% reduction in the adult worm burden or of the number developing larvae was considered significant activity. A program was devised to aid in making the following calculations: (1) the mean microfilaremia level for each test group, compared with that of the sham-dosed control; (2) the percent recoveries of adult *A. viteae* and *B. pahangi* in each test group as compared with those of the sham-dosed control (the individual percent recovery of each parasite is transformed to arc-sin values before analysis); and (3) the percent change in microfilaremia from day 0 to day 4 and from day 0 the day 56 was calculated for each group. Also, the daily percent weight change from day 0 through 4 was calculated. Active compounds were further evaluated against combined infections to determine the minimum effective dose and, if the compound was active against microfilariae, to obtain more information on its microfilaricidal activity by determining microfilaremia levels on day 0, 1, 3, 7, 21, 35, 42, and 56. In addition, an estimate of the therapeutic indices of an active compound was obtained when possible. Such an index was obtained by dividing the maximum tolerated dose of drug by the minimum dose with significant activity. Thus, in this system a compound could have three therapeutic indices: (1) one for *A. viteae* microfilariae; (2) one for *A. viteae* adults; and (3) one for *B. pahangi* adults.

Test Results

Several tests have been made to determine the activity of the compounds of this invention. In order to guide one of ordinary skill in the practice of the invention, these tests are described below, as well as results obtained in each test with a representative sampling of compounds. 2-Acetylpyridine thiosemicarbazones appear in the Table which follows the statement of utility section herein.

Relative to the Table, there were no toxic deaths or loss of weight of the jirds as a result of treatment with Filarizone (BK49685) or its analogs. No apparent toxic or sensitizing dermal reactions to any of the compounds were noted at the site of inoculation when tested subcutaneously. Table II shows the chemotherapeutic activity of Filarizone (BK49685). At a dose of 100 mg/kg/day×5 Filarizone (BK49685) killed 100% of the macrofilaria and microfilaria when given subcutaneously. More significantly, 100% filaricidal activity was observed against both filariae species.

EXAMPLE 1

2-Acetylpyridine 4-allyl-3-thiosemicarbazone (Procedure C)

A solution of 2.7 g (0.02 mol) of 2-acetylpyridine hydrazone in 5 ml of MeOH was treated with 3.1 g (0.03 mol) of allyl isothiocyanate and the solution was heated at reflux for 3 hours. The solution was cooled and the product which formed was collected. The crude material was recrystallized 3 times from MeOH, affording 2.5 g (49%) of white needles of 2-acetylpyridine 4-allyl-3-thiosemicarbazone, mp 107° C.

Analysis Calcd. for $C_{11}H_{14}N_4S$: C, 56.38; H, 6.02; N, 23.91; S, 13.68. Found: C, 56.09; H, 6.11; N, 24.36; S, 13.89.

EXAMPLE 2

2-Acetylpyridine 4-cyclohexyl-3-thiosemicarbazone (Procedure C)

A solution of 6.76 g (0.05 mol) of 2-acetylpyridine hydrazone in 10 ml of MeOH was treated with 7.2 g (0.05 mol) of cyclohexyl isothiocyanate and the solution was heated at reflux for 3 hours. The solution was chilled, and the crystals which formed were collected. Recrystallization of the product from 150 ml of MeOH afforded 6.40 9 (46%) of white needles of 2-acetylpyridine 4-cyclohexyl-3-thiosemicarbazone, mp 155° C.

Analysis Calcd for $C_{14}H_{20}N_4S$: C, 60.84; H, 7.29; N, 20.27; S, 11.60. Found: C, 60.76; H, 7.19; N, 20.16; S, 11.73.

EXAMPLE 3

2-Acetylpyridine 4-(2-diethylaminoethyl)-3-thiosemicarbazone dihydrobromide (Procedure A)

By the application of the procedure of R. S. McElhinney [*J. Chem. Soc.* (C)], 950 (1966), 2-diethylaminoethyl isothiocyanate (bp 54°–55° C./1.5 mm Hg), was prepared in 20% yield.

Analysis Calcd. for $C_7H_{14}N_2S$: C, 53.12; H, 8.92; N, 17.70; S, 20.26. Found: C, 52.97; H, 8.76; N, 18.01; S, 20.47.

A solution of 1 g (0.063 mol) of 2-diethylaminoethyl isothiocyanate in 5 ml of MeCN was treated with 0.3 g (0.063 mol) of 85% hydrazine hydrate. The solution was heated at reflux for 10 minutes and the solvent was removed under reduced pressure. The residue was then recrystallized from $C_6H_6$ affording 750 mg (63%) of white needles of 4-(2-diethylaminoethyl)-3-thiosemicarbazide, mp 83°–83.5° C.

Analysis Calcd. for $C_7H_{18}N_4S$: C, 44.18; H, 9.53; N, 29.44 S, 16.85. Found: C, 44.19; H, 9.46; N, 29.56; S, 16.60.

A solution of 605 mg (5 mmol) of 2-acetylpyridine in 10 ml of MeCN was treated with 950 mg (5 mmol) of 4-(2-diethylaminoethyl)- 3-thiosemicarbazide and the solution was heated at reflux for 10 hours. The pH of the solution was adjusted to 6 with concentrated HBr and diluted with 15 ml of $Et_2O$. An oil which separated from solution soon solidified. Crystallization of this product from MeOH-MeCN afforded 1.42 g (64%) of yellow crystals of 2-acetylpyridine 4-(2-diethylaminoethyl)-3-thiosemicarbazone dihydrobromide, mp 231° C. dec.

Analysis Calcd. for $C_{14}H_{23}N_5S$. 2HBr: C, 36.93; H, 5.54; N, 15.38; S, 704. Found: C, 36.99; H, 5.52; n, 15.30; S, 7.07.

EXAMPLE 4

2-Acetylpyridine 4-(3-fluorophenyl)-3-thiosemicarbazone (Procedure A)

2-Acetylpyridine (2.0 g, 0.0165 mol) in 70 ml of EtOH and 2.78 g (0.015 mol) of 4-(3-fluorophenyl)-3-thiosemicarbazide (mp 152°–155° C.) were heated at reflux temperature for 4 hours. The solution was refrigerated overnight and the product was collected. Recrystallization from MeCN afforded 1.1 g (25%) of 2-acetylpyridine 4-(3-fluorophenyl)-3-thiosemicarbazone, mp 159°–160° C.

Analysis Calcd. for $C_{14}H_{13}FN_4S$: C, 58.32; H, 4.54; N, 19.43; S, 11.12. Found: C, 57.87; H, 4.70; N, 19.41; S, 11.08.

EXAMPLE 5

2-Acetylpyridine 4,4-diisobutyl-3-thiosemicarbazone (Procedure B)

A solution of 10 g (0.044 mol) of methyl 3-[1-(2-pyridinyl)ethylidene]hydrazinecarbodithioate in 25 ml of MeOH was treated with 7.5 g (0.058 mol) of diisobutylamine and heated at reflux for 6 hours. The solution was chilled and the crystals which formed were collected. Recrystallization from 130 ml of heptane afforded 8.6 g (64%) of yellow needles of 2-acetylpyridine 4,4-diisobutyl-3-thiosemicarbazone, mp 96° C.

Analysis Calcd. for $C_{16}H_{26}N_4S$: C, 62.71; H, 8.55; N, 18.28; S, 10.46. Found: C, 63.27; H, 8.50; N, 18.14; S, 10.21.

EXAMPLE 6

Azacycloheptane-1-thiocarboxylic acid 2-[1-(2-pyridinyl)ethylidene]hydrazide (Procedure B)

A solution of 5.0 g (0.022 mol) of methyl 3-[1-(2-pyridyl)ethylidene]hydrazinecarbodithioate in 15 ml of MeOH was treated with 2.2 g (0.022 mol) of hexamethylenimine and heated at reflux for 5 hours. The solution was chilled, scratched and the product which separated was collected. Recrystallization from 150 ml of MeOH afforded 3.4 g (56%) of yellow needles of azacycloheptane-1-thiocarboxylic acid 2-[1-(2-pyridinyl)ethylidene]hydrazide, mp 165° C.

Analysis Calcd. for $C_{14}H_{20}N_4S$: C, 60.84; H, 7.29; N, 20.27 S, 11.60. Found: C, 60.91; H, 7.20; N, 20.30; S, 11.89.

EXAMPLE 7

3-Azabicyclo[3.2.2]nonane-3-thiocarboxylic acid 2-[1-(2-pyridinyl)ethylidene]hydrazide (Procedure B)

A solution of 3.8 g (0.018 mol) of methyl 3-[1-(2-pyridyl)ethylidene]hydrazinecarbodithioate and 2.1 g (0.017 mol) of 3-azabicyclo[3.2.2]nonane was heated at reflux for 5 hours. The solution was cooled, and the product which crystallized was collected. Recrystallization from 160 ml of MeOH afforded 3.34 g (65%) of yellow needles of 3-azabicyclo[3.2.2]nonane-3-thiocarboxylic acid 2-[1-(2-pyridinyl)ethylidene]hydrazide, mp 156° C.

Analysis Calcd. for $C_{16}H_{22}N_4S$: C, 63.54; H, 7.33; N, 18.53; S, 10.60. Found: C, 63.51; H, 7.25; N, 18.55; S, 10.67.

EXAMPLE 8

2-Acetylpyridine 4-cyclohexyl-4-methyl-3-thiosemicarbazone (Procedure B)

A solution of 10 g (0.44 mol) of methyl 3-[1-(2-pyridinyl)ethylidene]hydrazinecarbodithioate in 25 ml of MeOH was treated with 7.5 g (0.066 mol) of N-methylcyclohexylamine and the solution heated at reflux for 8 hours. The solution was cooled overnight and the product which crystallized was collected. Recrystallization from cyclohexane afforded 9.3 g (72%) of 2-acetylpyridine 4-cyclohexyl-4-methyl-3-thiosemicarbazone, mp 96° C.

Analysis Calcd. for $C_{15}H_{22}N_4S$: C, 62.03; H, 7.64; N, 19.29; S, 11.04 Found: C, 62.07; H, 7.74; N, 19.23; S, 11.14.

EXAMPLE 9

2-Acetylpyridine 4-(2-methylbenzyl)-3-thiosemicarbazone (Procedure B)

Methyl 3-[1-(2-pyridinyl)ethylidene]hydrazinecarbodithioate (4.51 g, 0.02 mol) and 3.64 g (0.03 mol) of 2-methylbenzylamine in 25 ml of methanol were heated under reflux for 36 hours followed by overnight refrigeration. The solid material which separated from solution was collected by filtration and recrystallized 3 times from ethanol to afford 2.85 g (48%) of white crystalline 2-acetylpyridine 4-(2-methylbenzyl)-3-thiosemicarbazone having a melting point of 152°-154° C.

Analysis Calcd. for $C_{16}H_{18}N_4S$: C, 64.40; H, 6.08; N, 18.78; S, 10.74. Found: C, 64.17; H, 6.23; N, 19.14; S, 10.64.

EXAMPLE 10

4-(2-Pyridinyl)-1-piperazinethiocarboxylic acid 2-[1-(2-pyridinyl)ethylidene]hydrazide (Procedure B)

Methyl 3-[1-(2-pyridinyl)ethylidene]hydrazinecarbodithioate (3.60 g, 0.016 mol) in 40 ml of EtOH was combined with 3.60 g (0.02 mol) of 1-(2-pyridinyl)piperazine. The solution was heated at reflux for 18 hours, cooled and the yellow product which separated was collected. Recrystallization from MeCN afforded 3.45 g (60%) of 4-(2-Pyridinyl)-1-piperazinethiocarboxylic acid 2-[1-(2-pyridinyl)ethylidene]hydrazide, mp 187°-188° C.

Analysis Calcd. for $C_{17}H_{20}N_6S$: C, 59.98; H, 5.92; N, 24.69; S, 9.42. Found: C, 60.65; H, 5.90; N, 24.61; S, 9.41.

EXAMPLE 11

2-Acetylpyridine 4-(2-pyridinyl)-3-thiosemicarbazone (Procedure A)

4-(2-Pyridinyl)-3-thiosemicarbazone (1.68 g, 0.01 mol) in 125 ml of EtOH and 7.5 ml of glacial acetic acid was treated with 1.21 g (0.01 mol) of 2-acetylpyridine. The solution was heated at reflux for 3 hours, cooled and the product was collected. Recrystallization from MeOH afforded 1.8 g (66%) of 2-Acetylpyridine 4-(2-pyridinyl)-3-thiosemicarbazone, mp 185°-187° C. dec.

Analysis Calcd. for $C_{13}N_{13}N_5S$: C, 57.54; H, 4.83; N, 25.81; S, 11.82. Found: C, 57.03; H, 5.08; N, 25.96; S, 12.17.

EXAMPLE 12

2-Acetylpyridine 4-(1-adamantyl)-3-thiosemicarbazone (Procedure A)

A solution of 1.5 g (0.03 mol) of hydrazine hydrate in 50 ml of EtOH was treated with 3.86 g (0.02 mol) of 1-adamantyl isothiocyanate, and stirred for one hour at room temperature. The product was collected and washed two times with EtOH, affording 4.33 g (96%) of 4-(1-adamantyl)-3-thiosemicarbazide, mp 206°-207° C. This thiosemicarbazide is disclosed in Chemical Abstracts, 70:11223 (1969); and in U.S. Pat No. 3,406,180.

2-Acetylpyridine (2.65 g, 0.022 mol) in 50 ml of EtOH and 2 ml of glacial acetic acid was combined with 4.33 g (0.0195 mol) of 4-(1-adamantyl)-3-thiosemicarbazone, and the solution was heated at reflux for 24 hours. The solution was cooled and the product was collected. Recrystallization from MeCN afforded 3.63 g (50%) of 2-acetylpyridine 4-(1-adamantyl)-3-thiosemicarbazone, mp 172°-173° C.

Analysis Calcd. for $C_{18}H_{24}N_4S$: C, 65.82; H, 7.36; N, 17.06; S, 9.76. Found: C, 66.04; H, 7.22; N, 16.88; S, 9.71.

EXAMPLE 13

2-Acetylpyridine 4,4-dimethyl-3-thiosemicarbazone (Procedure A)

To a solution of 2.39 g (0.02 mol) of 4,4-dimethyl-3-thiosemicarbazone in 75 ml of EtOH was added 2.54 g (0.021 mol) of 2-acetylpyridine. After heating at reflux for eight hours, the solution was cooled and the product was collected. Recrystallization from MeOH afforded 1.2 g (26%) of 2-acetylpyridine 4,4-dimethyl-3-thiosemicarbazone, mp 149°–150° C. dec.

Analysis Calcd. for $C_{10}H_{14}N_4S$: C, 54.03; H, 6.35; N, 25.20; S, 14.42. Found: C, 53.83; H, 6.74; N, 25.25; S, 14.72.

EXAMPLE 14

2-Acetylpyridine 4,4-dimethyl-3-thiosemicarbazone (Procedure B)

Methyl 3-[1-(2-pyridinyl)ethylidene]hydrazinecarbodithioate (9.02 g, 0.04 mol) in 30 ml of EtOH was combined with 5.2 g (0.08 mol) of dimethylamine (40% aqueous solution). The resulting solution was heated at reflux for 24 hours and the excess dimethylamine as removed under water-pump aspiration for 15 minutes. The solution was filtered and cooled to give 7.3 g (82%) of bright yellow crystals of 2-acetylpyridine 4,4-dimethyl-3-thiosemicarbazone, mp 155°–156° C. whose infrared spectrum was identical to that of the product made by the method described in Example 13.

EXAMPLE 15

1-Azacycloheptane-1-thiocarboxylic acid 2-[1-(2-pyridinyl)propylidene]hydrazide (Procedure B)

Methyl 3-[1-(2-pyridinyl)propylidene]hydrazinecarbodithioate (4.77 g, 0.02 mol) 2nd 3.4 ml (3.0 g, 0.03 mol) of hexamethylenimine in 25 ml of MeOH were heated under reflux for 48 hours followed by overnight refrigeration. The solid material which separated from solution was collected by filtration and recrystallized from MeOH to afford 3.65 g (63%) of yellow crystalline 1-azacycloheptane-1-thiocarboxylic acid 2-[1-(2-pyridinyl)propylidene]hydrazide, mp 117°–119° C.

Analysis Calcd. for $C_{15}H_{22}N_4S$: C, 62.03; H, 7.64; N, 19.29; S, 11.04. Found: C, 62.14; H, 7.64; N, 19.14; S, 11.16.

EXAMPLE 16

N-(2-Aminophenyl)-2-1-(2-pyridinyl)ethylidene]hydrazinecarbothioamide (Filarizone):

o-Phenylenediamine (4.32 g, 0.04 mole) and S-methyl 2-[1-(2-pyridinyl)ethylidene]hydrazinecarbothioamide (9 g, 0.04 mole) were heated under reflux in 150 ml of 95% EtOH for 24 hours. The solvent was evaporated under the reduced pressure to half of the original volume and the mixture was cooled. The brownish crystals which formed were collected and recrystallized from EtOH-$CHC_3$ to give 4.2 g (40%) of white crystals, mp 185°–187° C.

Analysis Calcd. for $C_{14}H_{15}N_5S$: C, 58.92; H, 5.30; N, 24.54; S, 11.24. Found: C, 59.01; H, 5.33; N, 24.86; S, 11.06.

STATEMENT OF UTILITY

The composition of this invention possess medicinal activity. More specifically, evidence indicates that all the compositions and their pharmaceutically-acceptable acid addition salts are active against macro- and/or microfilariae.

TABLE

Activity of heterocyclic and aromatic thiosemicarbazones against filaria $R_3-\overset{CH_3}{\underset{}{C}}=NNH-\overset{S}{\underset{N_1}{\overset{\|}{C}}}-N_1$

| Code no. | $R_3$ | $N_1$ | Dose. mg/kg/day (5 days) | % Suppression Macrofilaria | | % Suppression Microfilaria (A. vitae) | |
|---|---|---|---|---|---|---|---|
| | | | | Brugia pahangi | Acanth. vitae | 4 days | 56 days |
| BK49685 | 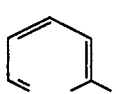 | 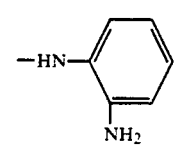 | 100<br>50<br>25<br>12.5 | 100<br>100<br>100<br>16 | 100<br>100<br>94<br>28 | 50<br>0<br>0<br>0 | 100<br>100<br>100<br>0 |
| BL55884 (HCl salts) | 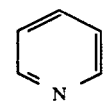 | 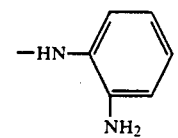 | 100<br>50<br>25<br>12.5 | 100<br>100<br>100<br>29 | 100<br>100<br>100<br>36 | 0<br>0<br>0<br>0 | |
| BH13318 | 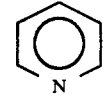 | 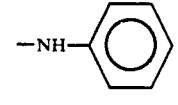 | 50<br>25 | 97<br>17 | 25<br>44 | 33<br>0 | |
| BK49676 | 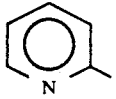 | —NHCH$_2$CH$_2$NH$_2$ | 25<br>12.5 | 26<br>−3 | 72<br>−40 | 67<br>67 | |
| BK56591 | 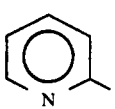 | —NH$_2$ | 100<br>1.56<br>12.5 | toxic<br>41<br>53 | 60<br>42 | 33<br>0 | |

TABLE-continued

Activity of heterocyclic and aromatic thiosemicarbazones against filaria $$R_3-\underset{\underset{CH_3}{|}}{C}=NNH-\underset{\underset{N_1}{|}}{\overset{\overset{S}{\|}}{C}}-N_1$$

| Code no. | R₃ | N₁/N₁ | Dose. mg/kg/day (5 days) | % Suppression Macrofilaria Brugia pahangi | Acanth. vitae | Microfilaria (A. vitae) 4 days | 56 days |
|---|---|---|---|---|---|---|---|
| BK46371 | 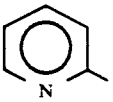 | 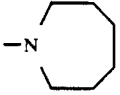 | 100<br>25<br>12.5 | toxic<br>84<br>100 | 100<br>−16 | 0<br>0 | |
| BH96013 | 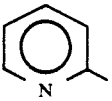 | 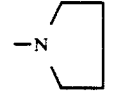 | 12.5<br>1.56 | 86<br>46 | 31<br>— | 0<br>— | |
| BH78604 | 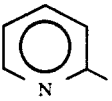 | 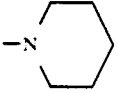 | 12.5<br>6.25 | 65<br>18 | 14<br>25 | 0<br>−100 | |
| BH13961 | 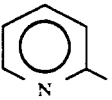 | 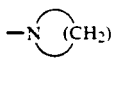 | 50 | 16 | 74 | 0 | |
| BK50115 (tetrahydrochloride salt) | 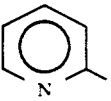 | 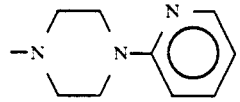 | 6.25<br>1.56 | −5<br>— | 100<br>40 | 50<br>83 | |
| BH86400 | 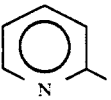 | 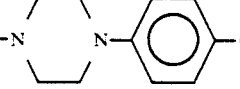 | 100<br>25 | 14<br>6 | 85<br>21 | 50<br>0 | |
| BK72933 | 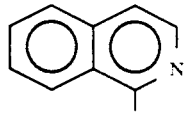 | 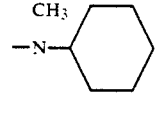 | 12.5 | 78 | 20 | −67 | |
| BK15447 | 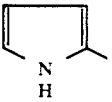 | 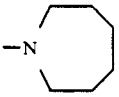 | 100 | 0 | 46 | 75 | |
| BK15438 | 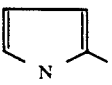 | 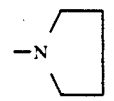 | 100 | 3 | 74 | 83 | |
| BK17441 | 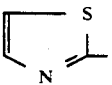 | 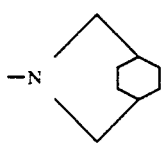 | 100 (X4)<br>25 (X5) | 67<br>8 | 60<br>20 | 0<br>86 | |
| BK52119 | 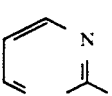 | 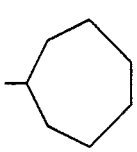 | 100 (X2) | 41 | 80 | 0 | |

TABLE-continued

Activity of heterocyclic and aromatic thiosemicarbazones against filaria

| Code no. | R$_3$ | $\underset{\underset{N_1}{|}}{R_3-\overset{\overset{CH_3}{|}}{C}=NNH-\overset{\overset{S}{\|}}{C}-N_1}$ | Dose. mg/kg/day (5 days) | % Suppression Macrofilaria | | % Suppression Microfilaria (A. vitae) | |
|---|---|---|---|---|---|---|---|
| | | | | Brugia pahangi | Acanth. vitae | 4 days | 56 days |
| BL52119 | 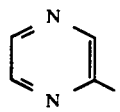 | —NH$_2$ | 100 | 62 | 60 | 50 | |
| | | | 25 | 6 | 40 | 50 | |
| BH67290 | 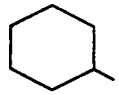 | 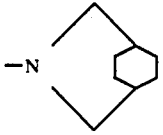 | 6.25 | 11 | 70 | 0 | |

We claim:

1. A composition of matter useful for the treatment of filariasis in an animal comprising a therapeutically effective amount of:
   (a) a thiosemicarbazone selected from the compounds represented by the formula

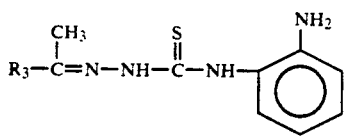

(b) a pharmaceutically-acceptable acid addition salt thereof wherein R$_3$ is pyridinyl; pyrrolyl; quinolyl; thiazyl; 1,3-diazinyl; 1,4-diazinyl and phenyl; and
   (c) a pharmaceutically-acceptable suspension medium (vehicle).

2. The composition of claim 1 wherein the vehicle comprises 0.5% hydroxyethyl cellulose and 0.1% Tween in an amount of from 95 to 99.9% by weight.

3. The composition of claim 1 wherein R$_3$ is selected from the group consisting of

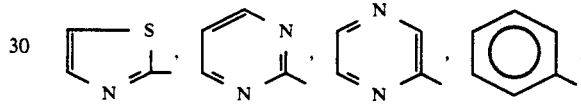

4. The composition of claim 3 wherein R$_3$ is

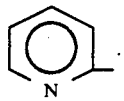

5. A method of systemically treating filarial infection in an animal comprising administering to said animal a therapeutically-effective amount of a composition of claim 1.

6. A method in accordance with claim 5 wherein the systemic treatment is effected prior to infection.

7. A method in accordance with claim 5 wherein the systemic treatment is effected subsequent to infection.

* * * * *